(12) United States Patent
Yamauchi

(10) Patent No.: US 6,879,399 B2
(45) Date of Patent: Apr. 12, 2005

(54) MEASURING METHOD FOR IMMUNOCHROMATOGRAPHIC TEST STRIP

(75) Inventor: Kazunori Yamauchi, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 0 days.

(21) Appl. No.: 10/257,270

(22) PCT Filed: Apr. 6, 2001

(86) PCT No.: PCT/JP01/02991

§ 371 (c)(1),
(2), (4) Date: Oct. 10, 2002

(87) PCT Pub. No.: WO01/77680

PCT Pub. Date: Oct. 18, 2001

(65) Prior Publication Data

US 2003/0160958 A1 Aug. 28, 2003

(30) Foreign Application Priority Data

Apr. 12, 2000 (JP) .................................. P2000-111137

(51) Int. Cl.$^7$ ............................................. G01N 21/00
(52) U.S. Cl. ...................... 356/344; 356/409; 356/432
(58) Field of Search ...................... 356/344, 39, 402, 356/409, 432

(56) References Cited

U.S. PATENT DOCUMENTS 5,572,287 A    11/1996  Wangler et al. ............... 355/53
5,770,389 A  * 6/1998  Ching et al. ............... 435/7.92

FOREIGN PATENT DOCUMENTS

| EP | 0 415 164 A1 | | 3/1991 | |
|----|----|----|----|----|
| JP | 48-18273 | * | 6/1973 | ............. G01J/1/02 |
| JP | 61-262635 | | 11/1986 | |
| JP | 1-313743 | * | 12/1989 | .......... G01N/21/88 |
| JP | 6-250137 | | 9/1994 | |
| JP | 7-5110 | | 1/1995 | |
| JP | 08334511 | | 12/1996 | |
| JP | 11-84529 | | 3/1999 | |
| JP | 2000-121562 | | 4/2000 | |
| WO | WO 95/13531 | * | 5/1995 | .......... G01N/21/86 |

* cited by examiner

Primary Examiner—Gregory J. Toatley, Jr.
Assistant Examiner—Roy M. Punnoose
(74) Attorney, Agent, or Firm—Morgan, Lewis & Bockius LLP

(57) ABSTRACT

A measuring device includes an irradiation optical system and a detection optical system. The irradiation optical system includes a light-emitting element and a mixing rod. The detection optical system includes a lens and an imaging element. Light from the light-emitting element enters into the mixing rod, where it is mixed. The light mixed inside the mixing rod is irradiated onto an immunochromatography test piece as measurement light. The light transmitted by the immunochromatography test piece is formed as an image on an acceptance surface of the imaging element, by means of the lens. The imaging element captures the image formed by the lens at the acceptance surface.

2 Claims, 7 Drawing Sheets

MEASURING METHOD FOR IMMUNOCHROMATOGRAPHIC TEST STRIP

TECHNICAL FIELD

The present invention relates to a device for measuring immunochromatography test pieces.

BACKGROUND ART

In immunochromatography analysis, antibodies (or antigens) which provoke a antigen or antibody reaction with antigens (or antibodies) in a subject (sample) are previously coated in strips onto prescribed positions of an immunochromatography test piece. After applying a subject to an immunochromatography test piece, the antigens (or antibodies) in the subject are dissolved out using a developer solution, and are caused to impregnate into the immunochromatography test piece, whereupon the antigens (or antibodies) in the subject are trapped by an antigen or antibody reaction in the region of the antigens (or antibodies) coated onto the immunochromatography test piece. Since the quantity trapped is the total amount of that antigen (or antibody) in the subject, it is possible to measure the total amount of the antigen (or antibody) by means of optical measurement, such as light absorption, or the like, if the antigen (or antibody) in the subject is previously marked by a dye. Immunochromatography analysis can be used for measuring extremely small quantities, compared to standard calorimetric methods.

Japanese Patent Laid-open No. H7-5110 discloses a measuring device for measuring the concentration of a specific material in a subject from an immunochromatography test piece after development and dying of the subject. In the measuring device described in Japanese Patent Laid-open No. H7-5110, light from an LED is irradiated onto an immunochromatography test piece, the light reflected from the immunochromatography test piece is detected by a CCD color image sensor, and the degree of coloration is identified.

DISCLOSURE OF THE INVENTION

However, if a light-emitting element, such as an LED, is used as the light source of the measuring device, then the amount of light irradiated onto the immunochromatography test piece is low, and since the colored region of the immunochromatography test piece is very small (approximately 0.5 mm), it is difficult to detect the colored region. In order to increase the amount of light irradiated onto the immunochromatography test piece, the use of a light-emitting tube, such as a sodium tube, fluorescent tube, or the like, for the light source, has been considered, but in such cases, the device would become large in size.

The present invention was devised with the foregoing in view, an object thereof being to provide a measuring device for immunochromatography test pieces whereby detection of colored regions of an immunochromatography test piece can be performed reliably, without increasing the size of the device.

In order to achieve the aforementioned object, the measuring device for immunochromatography test pieces according to the present invention is a measuring device for immunochromatography test pieces, comprising an irradiation optical system for irradiating measurement light onto immunochromatography test pieces; and a detection optical system for detecting light from the immunochromatography test pieces due to irradiation of the measurement light; characterized in that the irradiation optical system comprises a light-emitting element, and a mixing rod for mixing the light output from the light-emitting element, the light exiting from the mixing rod being irradiated onto the immunochromatography test piece as the measurement light; and the detection optical system comprises an imaging lens for forming an image of the light from the immunochromatography test piece, and an imaging element disposed in a position where the light from the immunochromatography test piece is formed into an image by the imaging lens, the light transmitted by the immunochromatography test piece being detected by the imaging element.

Thus, an irradiation optical system and a detection optical system are provided, the irradiation optical system comprising a light-emitting element, and a mixing rod for mixing the light output from the light-emitting element, the light exiting from the mixing rod being irradiated onto the immunochromatography test piece as the measurement light; and the detection optical system comprising an imaging lens for forming an image of the light from the immunochromatography test piece, and an imaging element disposed in a position where the light from the immunochromatography test piece is formed into an image by the imaging lens, the light from the immunochromatography test piece being received and detected by the imaging element. Since the light output by the light-emitting element is mixed by the mixing rod and then irradiated onto the immunochromatography test piece, attenuation of light by the light-emitting element is suppressed, and the amount of light irradiated onto the immunochromatography test piece is increased. Consequently, the colored portion of the immunochromatography test piece can be detected reliably by the imaging element. Moreover, since a light-emitting element is used as a light source, it is possible to suppress increase in the size of the device.

The measuring device for immunochromatography test pieces according to the present invention may also be characterized in that diffusing means for diffusing the light input to the mixing rod and the light exiting from the mixing rod are further provided on the light input side and light output side of the mixing rod.

By further providing diffusing means for diffusing the light input to the mixing rod and the light exiting from the mixing rod on the light input side and light output side of the mixing rod, the light irradiated onto the immunochromatography test pieces is approximately equalized. Thereby, the colored region of the immunochromatography test pieces can be detected with even greater reliability by the imaging element.

Furthermore, the measuring device for immunochromatography test pieces according to the present invention may also be characterized in that the immunochromatography test piece is held in a casing having an observation window; the irradiation optical system irradiating the light emitted from the mixing rod towards the observation window, as the measurement light; and the surface area of the light output face of the mixing rod being set to a larger area than the surface area of the observation window.

The immunochromatography test piece is held in a casing having an observation window and the irradiation optical system irradiates the light emitted from the mixing rod as measurement light onto the observation window, and since the surface area of the light output face of the mixing rod is greater than the surface area of the observation window, the light irradiated onto the position corresponding to the observation window of the immunochromatography test piece is approximately equalized. Thereby, the colored region of the immunochromatography test piece can be detected with even greater reliability by the imaging element.

BEST MODES FOR CARRYING OUT THE INVENTION

Figure 1:
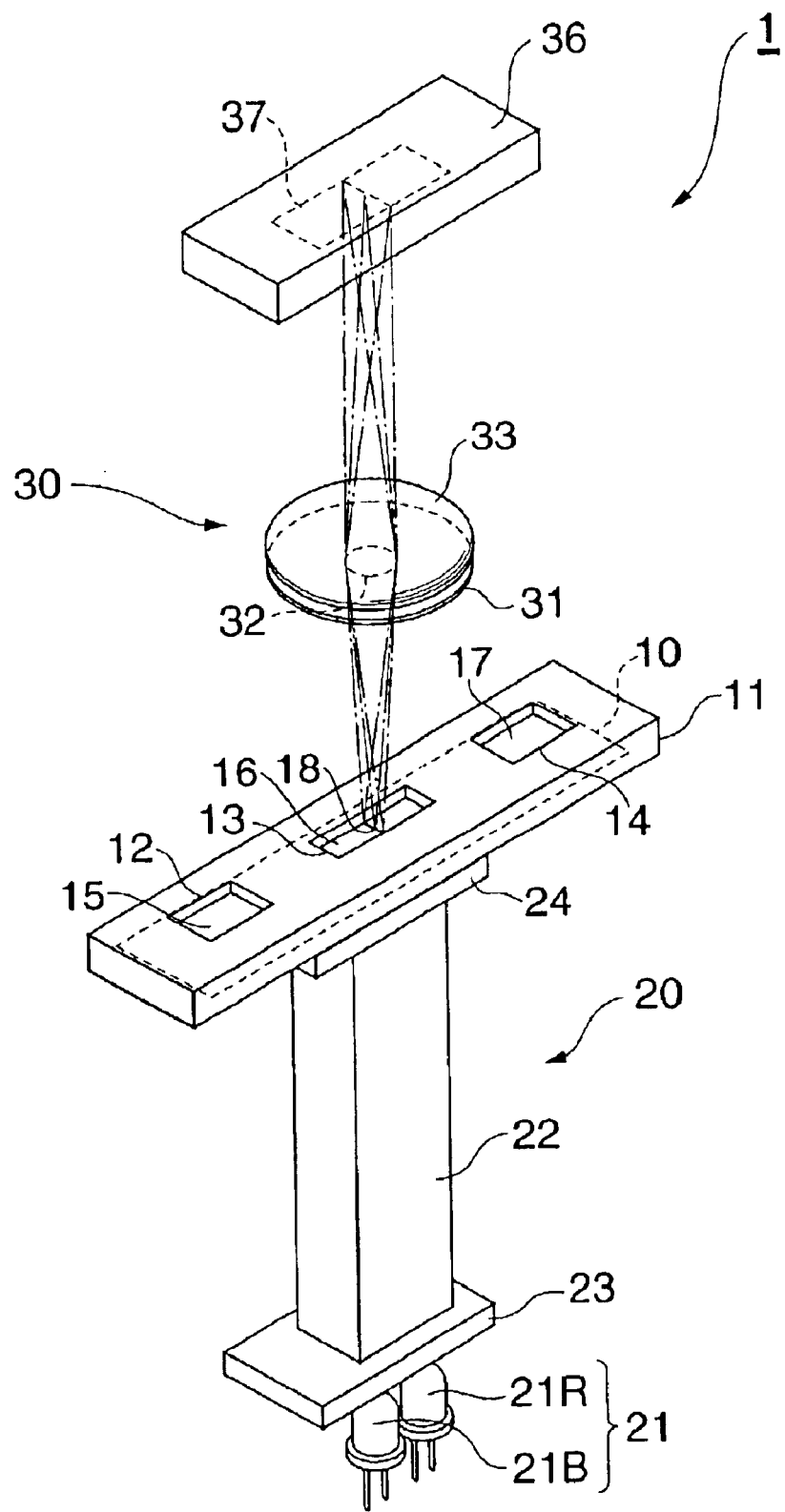
FIG. 1 is an approximate compositional diagram showing a measuring device for immunochromatography test pieces relating to a first embodiment of the present invention.

A measuring device for immunochromatography test pieces relating to embodiments of the present invention is now described with reference to the drawings. In the respective drawings, similar elements or elements having similar functions are similarly labelled, and duplicated description thereof is omitted.

(First Embodiment)

Firstly, a measuring device 1 for immunochromatography test pieces relating to a first embodiment is described.

The measuring device 1 comprises an irradiating optical system 20 for irradiating measurement light onto an immunochromatography test piece 10, and a detection optical system 30 for detecting light from an immunochromatography test piece 10 by irradiation of the measurement light. The irradiation optical system 20 comprises a light-emitting element 21 and a mixing rod 22. Moreover, the detection optical system 30 comprises an aperture 31, a convex lens 33 forming an imaging lens, and a CCD image sensor 36 forming an imaging element.

The immunochromatography test piece 10 has a long rectangular shape and is made from a material such as a nitrocellulose membrane, or filter paper, or the like. This immunochromatography test piece 10 is held inside a casing having a long rectangular shape in plan view, and a subject application window 12, observation window 13 and control window 14 are provided extending in the direction of the longer side in the casing 11. The immunochromatography test piece 10 comprises a subject application section 15 provided in a position corresponding to the subject application window 12, and detecting sections 16, 17 provided in positions corresponding to the observation window 13 and control window 14. The detecting section 16 has a line shape (or band shape) formed by coating respective antigens (or antibodies) which react with antigens (or antibodies) in the subject, and causing same to solidify. The casing 11 which holds the immunochromatography test piece 10 is held by holding means (not illustrated). The observation window 13 has a size of 4 mm×8 mm, for example.

The subject is applied dropwise via the subject application window 12 onto the subject application section 15 of the immunochromatography test piece 10. The antigens (or antibodies) in the subject couple with the indicator dye and the indicator dye coupled with the antigens (or antibodies) in the subject, as well as unreacted indicator dye, travel in the longitudinal direction of the immunochromatography test piece 10. Supposing that the subject contains antigens, then it is assumed that the antigens will undergo an antigen/antibody reaction with the respective detecting sections. As the subject travels, the antigens in the subject and the antigens fixed to the detecting section 16 react specifically and a line-shaped pattern 18 colored by the indicator dye is formed in the detecting section 16 which has reacted. This colored line-shaped pattern 18 is formed extending in a direction intersecting (for example, orthogonally) with the direction of travel of the antigens (or antibodies) of the subject in the immunochromatography test piece 10, and it can be observed by means of the observation window 13.

The light-emitting element 21 comprises a plurality of LEDs having different light emission wavelengths, in the present embodiment, a blue LED 21B and a red LED 21R. If the line-shaped pattern 18 formed by the antigen/antibody reaction is colored red, then the blue LED 21B is caused to emit light. If the line-shaped pattern 18 formed by the antigen/antibody reaction is colored blue, then the red LED 21R is caused to emit light.

The mixing rod 22 is a square-shaped (or circular-shaped) rod made from transparent acrylic resin for mixing the light output by the light-emitting element 21 (blue LED 21B or red LED 21R), and it has a light input face and a light output face at the respective ends thereof. The aforementioned light-emitting element 21 is positioned on the light input face side of the mixing rod 22. An immunochromatography test piece 10 (casing 11) is positioned on the light output face side of the mixing rod 22. More specifically, the immunochromatography test piece 10 (casing 11) is positioned opposing the light output face of the mixing rod 22 in such a manner that the observation window 13 of the casing 11 coincides with the light output face of the mixing rod 22. The light output face of the mixing rod 22 has a size of 8 mm×14 mm, and the surface area of the light output face of this mixing rod 22 is set to a larger area than the surface area of the opening in the observation window 13 of the casing 11.

Diffusion plates 23, 24 forming diffusing means are provided at the light input face and light output face of the mixing rod 22, in a state of contact with the light input face and light output face of the mixing rod 22. These diffusing plates 23, 24 are made from opaque acrylic resin. Instead of providing diffusing plates 23, 24, it is also possible to form the actual light input face and light output face of the mixing rod 22 into ground glass faces in order to provide diffusing means.

The light output from the light-emitting element 21 (blue LED 21B or red LED 21R) is diffused by the diffusing plate 23 and then enters into the mixing rod 22 via the light input face of the mixing rod 22. The light that has entered the mixing rod 22 is mixed by being fully reflected at the side faces of the mixing rod 22 whilst it is propagated therein, and this mixed light arrives at the light output face of the mixing rod 22. The light arriving at the light output face of the mixing rod 22 is diffused by the diffusing plate 24, and is then irradiated as measurement light from the rear face of the observation window 13 of the casing 11 in the direction of the immunochromatography test piece 10 (observation window 13 of the casing 11).

The aperture 31 has a restricting hole section 32. The transmission light that is transmitted through the immunochromatography test piece 10 (casing 11) due to irradiation of measurement light and exits from the observation window 13 is restricted by the restricting hole section 32 of the aperture 31. The convex lens 33 forms an image of the transmission light from the immunochromatography test piece 10 (casing 11) which is incident thereon via the restricting hole section 32 of the aperture 31.

The CCD image sensor 36 has a light receiving face 37, which is situated at the position where an image of the transmission light from the immunochromatography test piece 10 (casing 11) is formed by the convex lens 33. Light-receiving elements are provided in a one-dimensional or two-dimensional array on the light-receiving face 37. The CCD image sensor 36 detects the transmission light from the immunochromatography test piece 10 by capturing the image formed by the convex lens 33 on the light receiving face 37.

Figure 2:
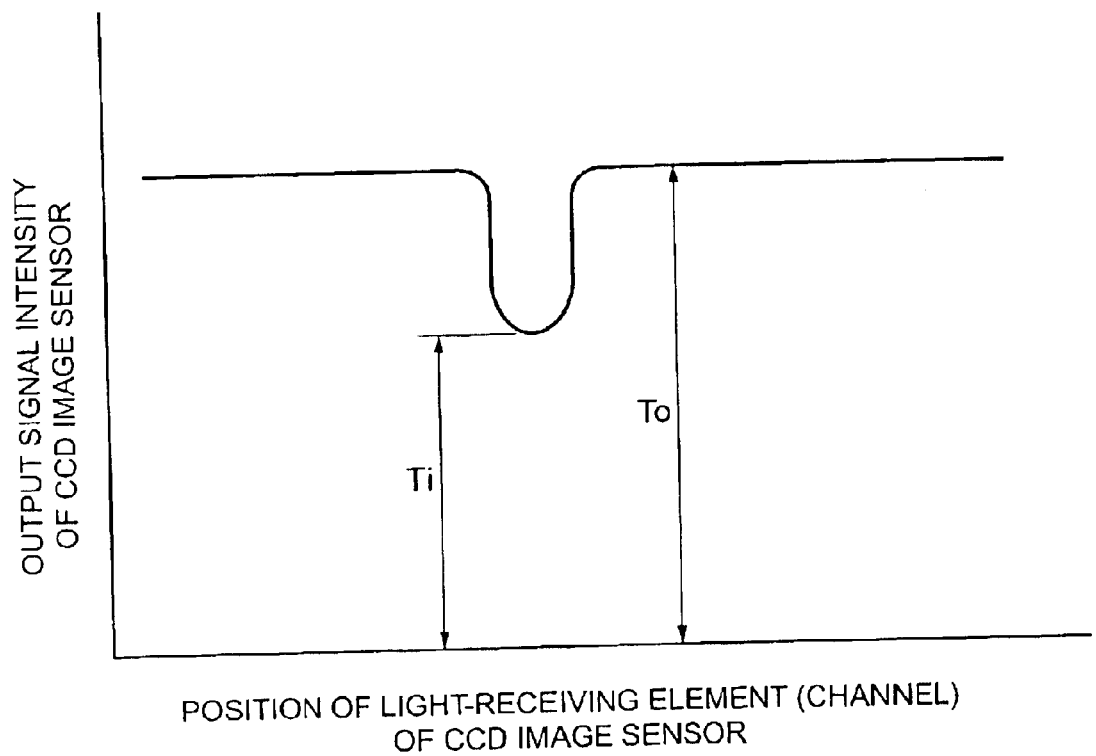
FIG. 2 is a graph showing the light absorption profile of light transmitted by an immunochromatography test piece.

Next, a method for determining the concentration of the subject is described. When transmission light from the immunochromatography test piece 10 is detected by the CCD image sensor 36, the light absorption of the line-shaped pattern 18 formed by coloration is determined as described below, on the basis of the output signal from the CCD image sensor 36. Firstly, a light absorption profile of the transmission light of the immunochromatography test piece 10 is created as illustrated in FIG. 2, on the basis of the output signal intensity from the CCD image sensor 36 and the position of the light-receiving element (channel) of the CCD image sensor 36. Thereupon, the light absorption ABS is calculated by means of the following equation (1), taking $T_o$ as the output signal intensity at a position in the created absorption profile corresponding to a portion of the immunochromatography test piece 10 that is not colored, and taking $T_i$ as the output light intensity at a position corresponding to a colored region thereof (line-shaped pattern 18).

$$ABS = \log (T_o/T_i) \tag{1}$$

When the light absorption ABS is calculated, the total quantity (concentration) of antibodies or antigens contained in the subjected is derived from the light absorption ABS, by referring to a previously created quantity characteristics graph.

It is also possible to calculate the light absorption ABS on the basis of the following equation (2), taking $T_{ao}$ as the average output signal intensity at a position of the created absorption profile corresponding to a region of the immunochromatography test piece that is not colored, and $T_{ai}$ as the average output signal intensity at a position corresponding to a color region (line-shaped pattern).

$$ABS = \log (T_{ao}/T_{ai}) \tag{2}$$

In this way, an irradiation optical system 20 and a detection optical system 30 are provided in the measuring device 1. The irradiation optical system 20 comprises a light-emitting element 21 (blue LED 21B or red LED 21R), and a mixing rod 22, and the light emitted from the mixing rod 22 is irradiated as measurement light onto the immunochromatography test piece 10 (casing 11). The detection optical system 30 comprises a convex lens 33 and CCD image sensor 36, and detects transmission light from the immunochromatography test piece 10 (casing 11) by means of the CCD image sensor 36. Since the light output by the light-emitting elements 21 is mixed by the mixing rod 22 before being irradiated onto the immunochromatography test piece 10 (casing 11), attenuation of the light from the light-emitting elements 21 is suppressed, and the amount of light irradiated onto the immunochromatography test piece 10 is increased. Consequently, the CCD image sensor 36 is able reliably to detect a line-shaped pattern 18 formed by coloration of the immunochromatography test piece 10. Moreover, since light-emitting elements 21 (a blue LED 21B and a red LED 21R) are used, it is possible to suppress increase in the size of the measuring device 1.

Furthermore, in the measuring device 1, since diffusing plates 23, 24 are provided at the light input face and light output face of the mixing rod 22, the light irradiated onto the immunochromatography test piece 10 (casing 11) is approximately equalized. Thereby, it is possible to perform detection of the line-shaped pattern 18 in the immunochromatography test piece 10 by means of the CCD image sensor 36 with even greater reliability.

Furthermore, in the measuring device 1, since the surface area of the light output face of the mixing rod 22 is greater than the surface area of the observation window 13 of the casing 11, the light irradiated onto a position corresponding to the observation window 13 of the immunochromatography test piece 10 will be further equalized. Thereby, the detection of the line-shaped pattern 18 in the immunochromatography test piece 10 by means of the CCD image sensor 36 can be performed with even greater reliability.

Moreover, the irradiation optical system 20 and detection optical system 30 in the measuring device 1 are positioned in such a manner that the CCD image sensor 36 receives the transmission light of the measurement light irradiated onto the immunochromatography test piece 10, and the light absorption of the line-shaped pattern 18 formed by coloration is measured on the basis of the transmission light received by the CCD image sensor 36. Thereby, the degree of coloration of the line-shaped pattern 18 formed in the immunochromatography test piece 10 can be measured simply and very accurately, and the total amount (concentration) of antigens or antibodies contained in the subject can be measured precisely.

(Second Embodiment)

Figure 3:
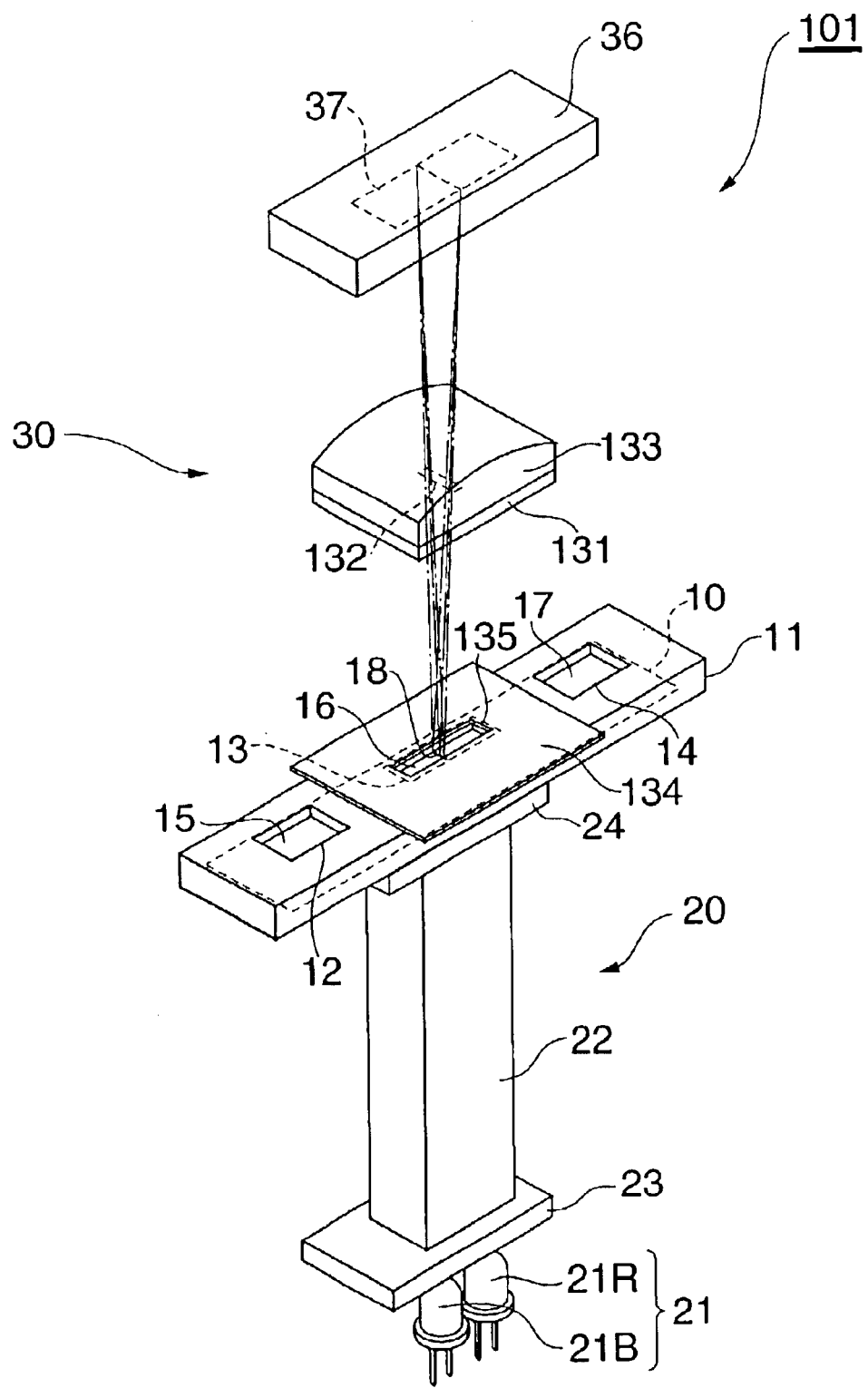
FIG. 3 is an approximate compositional diagram showing a measuring device for immunochromatography test pieces relating to a second embodiment.

Next, with reference to FIG. 3, the measuring device 101 for immunochromatography test pieces relating to a second embodiment of the present invention is described. The measuring device 101 relating to the second embodiment differs from the measuring device 1 relating to the first embodiment in that the imaging lens is a cylindrical lens.

The measuring device 101 comprises an aperture 131, and a cylindrical lens 133 forming an imaging lens. This cylindrical lens 133 is disposed in such a manner that the direction of the generating line of the curved face of the cylindrical lens 133 intersects (orthogonally, for example) with the direction of travel of the antigens (or antibodies) of the subject in the immunochromatography test piece 10, in other words, in such a manner that it faces the direction of extension of the line-shaped pattern 18 formed by coloration of the immunochromatography test piece 10.

The aperture 131 is disposed on the light input face side of the cylindrical lens 133. A long rectangular slit 132 extending in the direction of the generating line of the curved face of the cylindrical lens 133 is formed in this aperture 131.

An aperture 134 for restricting the input of light other than light from the observation window 13 to the cylindrical lens 133 is provided on the light output side of the immunochromatography test piece 10 (casing 11). A hole section 135 for passing transmission light from the immunochromatography test piece 10 (casing 11) is provided in the aperture 134.

The measuring device 101 having the foregoing composition provides the same action and beneficial effects as the measuring device 1 relating to the first embodiment and is able reliably to detect a line-shaped pattern 18 formed by coloration of an immunochromatography test piece 10, by means of the CCD image sensor 36. Moreover, since light-emitting elements 21 (blue LED 21B or red LED 21R) are used as light sources, it is possible to prevent increase in the size of the measuring device 101.

Moreover, the measuring device 101 has a cylindrical lens 133 as an imaging lens, and this cylindrical lens 133 is disposed so that the direction of the generating line of the curved face thereof intersects with the direction of travel of the antigens or antibodies in the immunochromatography test piece 10, and it forms an image of the line-shaped pattern 18 formed in a direction intersecting with the direction of travel of the antigens or antibodies, on the CCD image sensor 36, due to irradiation of measurement light. Thereby, light that is parallel to the direction of travel of the antigens or antibodies in the immunochromatography test piece 10 is formed as an image on the CCD image sensor 36, and light that is orthogonal to the direction of travel of the antigens or antibodies in the immunochromatography test piece 10 is defocused and equalized. Consequently, even if uneven coloration occurs in the direction of extension of the line-shaped pattern 18 formed by coloration of the immunochromatography test piece 10, this uneven coloration will be optically equalized by the cylindrical lens 133, and hence a pattern wherein uneven coloration is optically equalized will be formed as an image on the CCD image sensor 36. As a result, it is possible to measure the degree of coloration of the line-shaped pattern 18 formed on the immunochromatography test piece 10 to a high level of accuracy.

Moreover, since an aperture 131 formed with a long rectangular slit 132 extending in the direction of the generating line of the curved face of the cylindrical lens 133 is disposed on the light input face side of the cylindrical lens 133, it is possible to form an image having little aberration on at the CCD image sensor 36.

(Third Embodiment)

Next, a measuring device 201 for immunochromatography test pieces relating to a third embodiment is described on the basis of FIG. 4 to FIG. 9. The measuring device 201 relating to the third embodiment differs from the measuring device 101 relating to the second embodiment and second embodiment in that the light path is constituted in a bent fashion by using mirrors.

Figure 4:
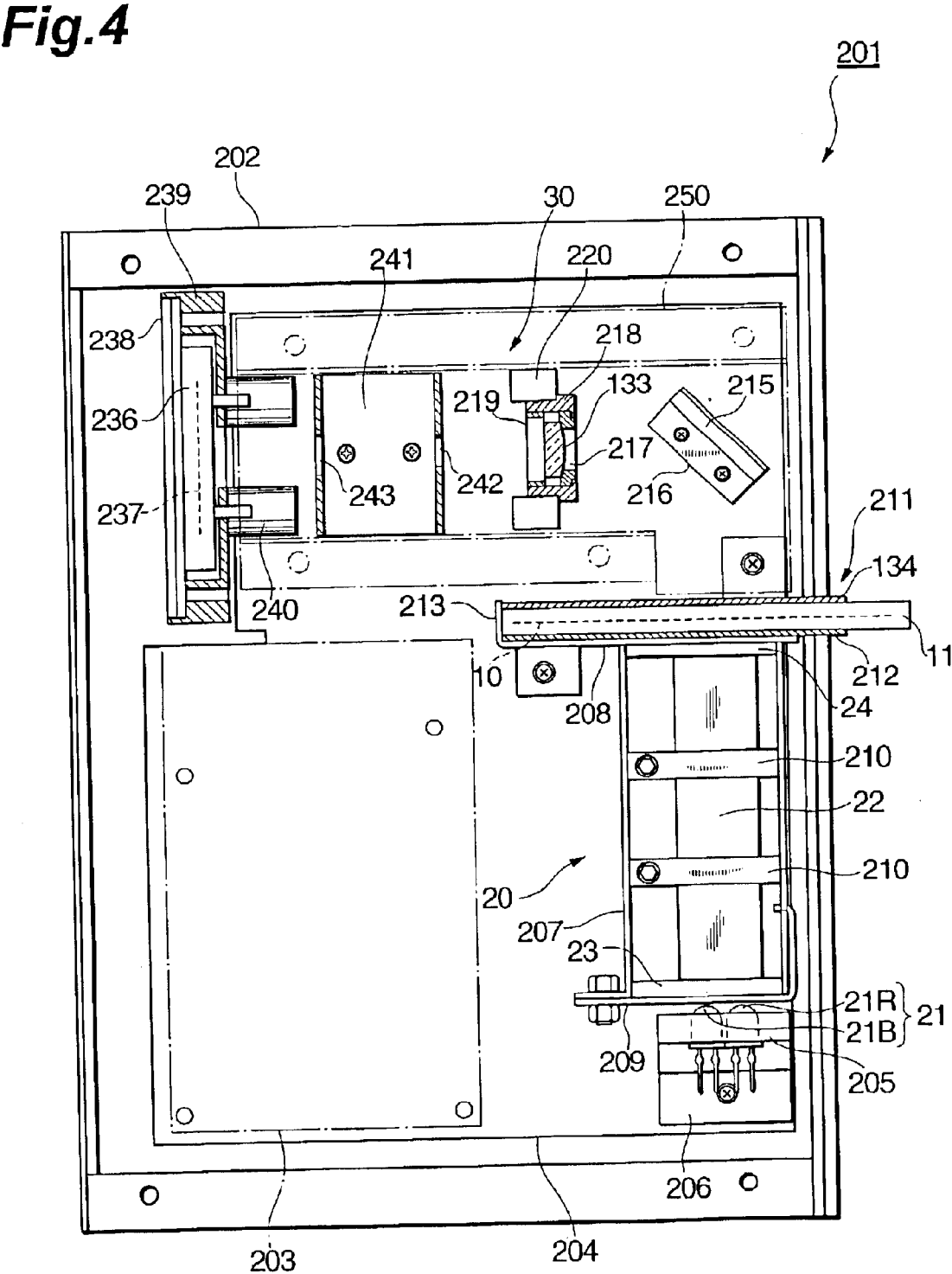
FIG. 4 is a side view of a measuring device for immunochromatography test pieces relating to a third embodiment of the present invention.
Figure 5:
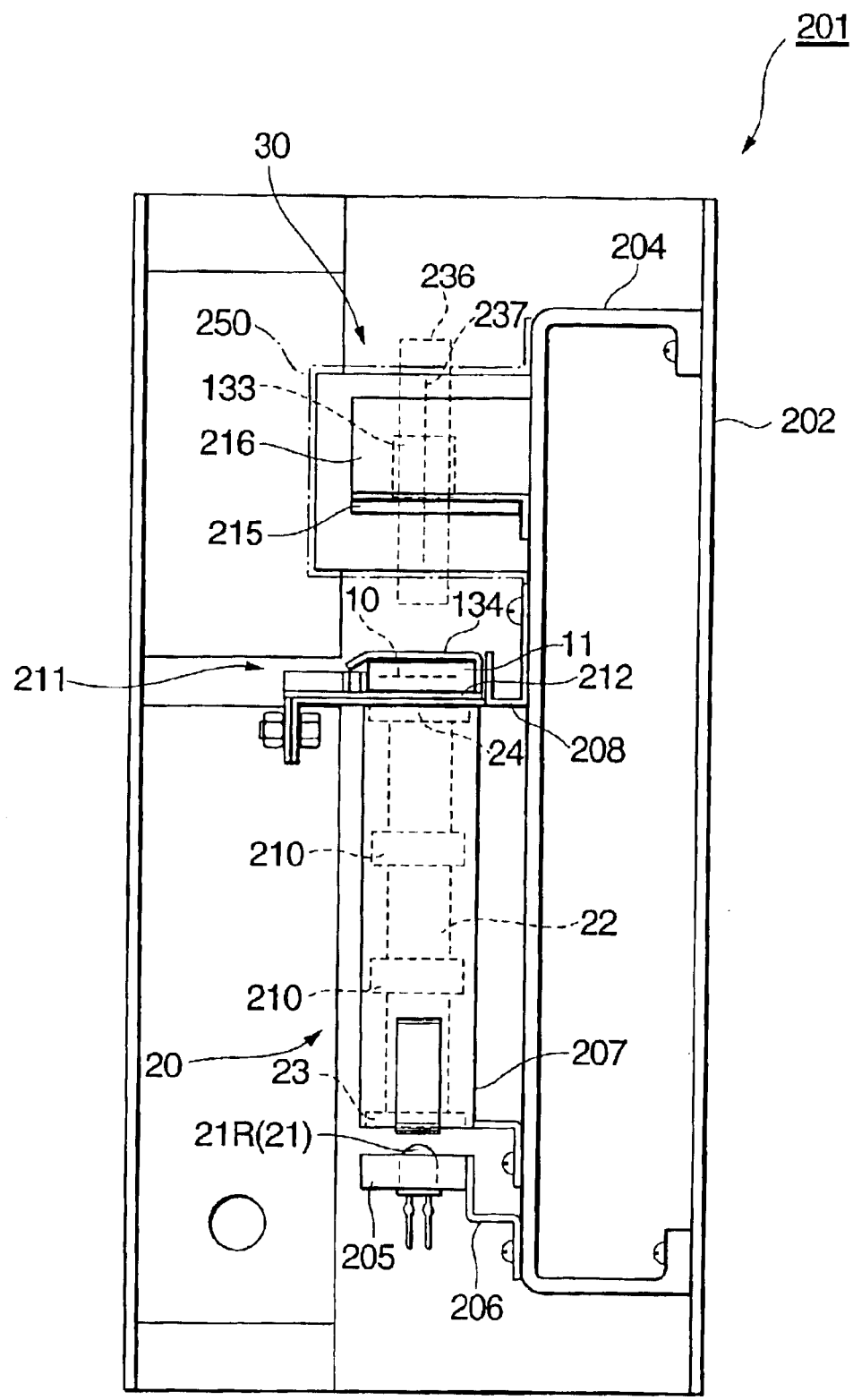
FIG. 5 is a front view of a measuring device for immunochromatography test pieces relating to a third embodiment of the present invention.

As shown in FIG. 4 and FIG. 5, the measuring device 201 comprises a case 202, and a lid (not illustrated) which fits onto the case 202. A chassis 204 is fitted inside the case 202 in order to position an irradiation optical system 20, a detection optical system 30, and a control circuit 203 for controlling the operation of the measuring device 201 by performing various calculation processes.

The light-emitting elements 21 (blue LED 21B or red LED 21R) are fixed to an installation plate 205, and this installation plate 205 is attached to the chassis 204 via a bracket 206.

A mixing rod 22 is situated inside a rod case 207, in a state whereby the light input face and light output face of the mixing rod 22 contact diffusion plates 23, 24. The position of the mixing rod 22 in the direction of the light guide is limited by means of a restricting section 208 formed integrally with the rod case 207 confronting the diffusion plate 24, and a rod pressing plate 209 combined with the rod case 207 confronting the diffusion plate 23. A plurality of rod holders 210 are installed on the side face of the mixing rod 22, at prescribed intervals in the light guide direction of the mixing rod 22. The position of the mixing rod 22 in the direction orthogonal to the light guide direction thereof is limited by means of these rod holders 210 confronting the side walls of the rod case 207.

A test piece holder 211 constituted so that an immunochromatography test piece 10 (casing 11) can be inserted therein, is provided on the upper face of the restricting section 208 (rear side of the face confronting the diffusion plate 24). This test piece holder 211 functions as holding means for holding the immunochromatography test piece 10 (casing 11).

The test piece holder 211 is constituted in such a manner that, the casing 11 makes contact with the aperture 134, when it is inserted inside the test piece holder 211 and positioned in a test piece installation section 212 formed integrally with the aperture 134. The test piece holder 211 is installed on the chassis 204 in a state where the restricting section 208 and test piece installation section 212 are in mutual contact. The insertion position of the immunochromatography test piece 10 (casing 11) in the longitudinal direction is restricted by means of a restricting section 213 formed integrally with the rod case 207 (restricting section 208) making contact with the end of the casing 11 in the longitudinal direction thereof.

Figure 6:
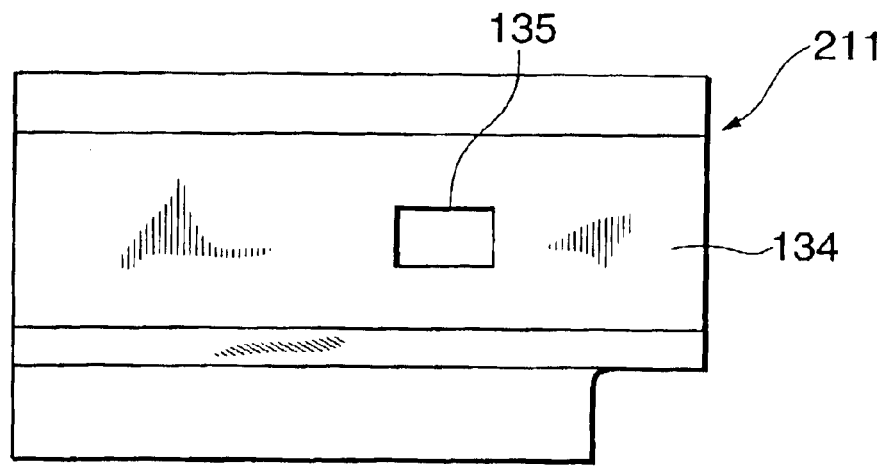
FIG. 6 is a plan view of a test piece holder included in a measuring device for immunochromatography test pieces relating to a third embodiment of the present invention.
Figure 7:
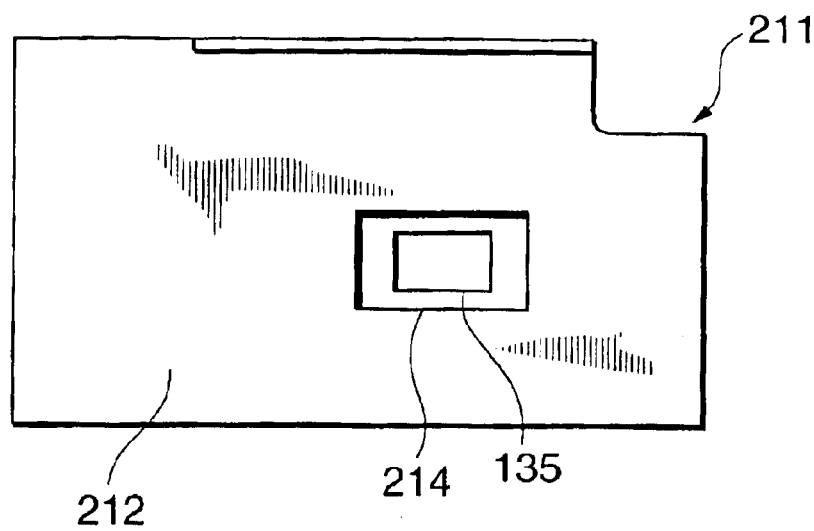
FIG. 7 is a rear view of a test piece holder included in a measuring device for immunochromatography test pieces relating to a third embodiment of the present invention.

As shown in FIG. 6, a hole section 135 for passing transmission light from the immunochromatography test piece 10 (casing 11) is provided in the aperture 134. The hole section 135 of the aperture 134 has a size of 5 mm×8 mm. Furthermore, as shown in FIG. 7, a hole section 214 for irradiating light from the diffusion plate 24 onto the immunochromatography test piece 10 (casing 11) is provided on the test piece installation section 212 of the test piece holder 211. The hole section 214 of the test piece installation section 212 has a size of 8 mm×14 mm. The light output face of the mixing rod 22 also has a size of 8 mm×14 mm. The observation window has a size of 4 mm×8 mm.

A mirror 215 is provided on top of the test piece holder 211. This mirror 215 is installed on the chassis 204 via a mirror holder 216. The light reflected by the mirror 215 is input to the cylindrical lens 133. The light path is bent in the measuring device 201 by means of this mirror 215, and as illustrated in FIG. 4, the irradiation optical system 20 and the detection optical system 30 are located in an inverse L shape. The control circuit 203 is installed on the chassis 204 in a position to the inner side of the irradiation optical system 20 and detection optical system 30 provided in an inverse L shape. By laying out the irradiation optical system 20, detection optical system 30 and control circuit 203 in this way, it is possible to achieve compactification of the measuring device 201.

Figure 8:
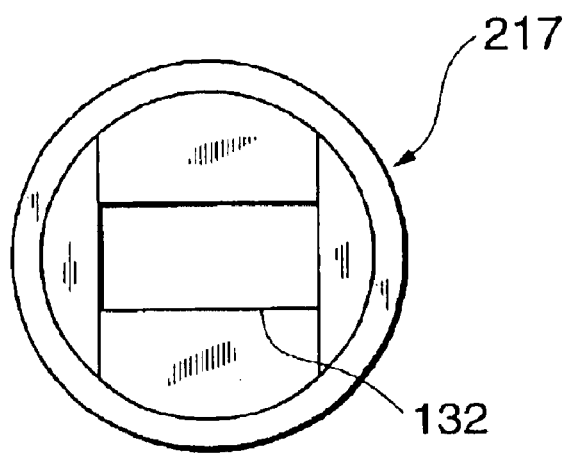
FIG. 8 is a plan view of a lens mask included in a measuring device for immunochromatography test pieces relating to a third embodiment of the present invention.

The cylindrical lens 133 is positioned in such a manner that the direction of the generating line of the curved face of the cylindrical lens 133 intersects (orthogonally, for example,) with the direction of travel of the antigens (or antibodies) of the subject in the immunochromatography test piece 10, in other words, in such a manner that it faces in the direction of extension of the line-shaped pattern 18 formed by coloration in the immunochromatography test piece 10. A lens mask 217 forming an aperture is positioned on the light input side of the cylindrical lens 133. As shown in FIG. 8, a long rectangular slit 132 extending in the direction of the generating line of the curved face of the cylindrical lens 133 is formed in the lens mask 217. The size of this slit 132 is set to 4 mm×8 mm.

The cylindrical lens 133 and lens mask 217 are held on either side by a lens holder 218 and pressing ring 219, by means of the lens holder 218 and pressing ring 219 being screw fitted together. The lens holder 218 is fixed in a state where it is inserted into a hole section of a lens installation tube 220. The lens installation tube 220 with the lens holder 218 fixed thereto is installed on the chassis 204.

Figure 9:
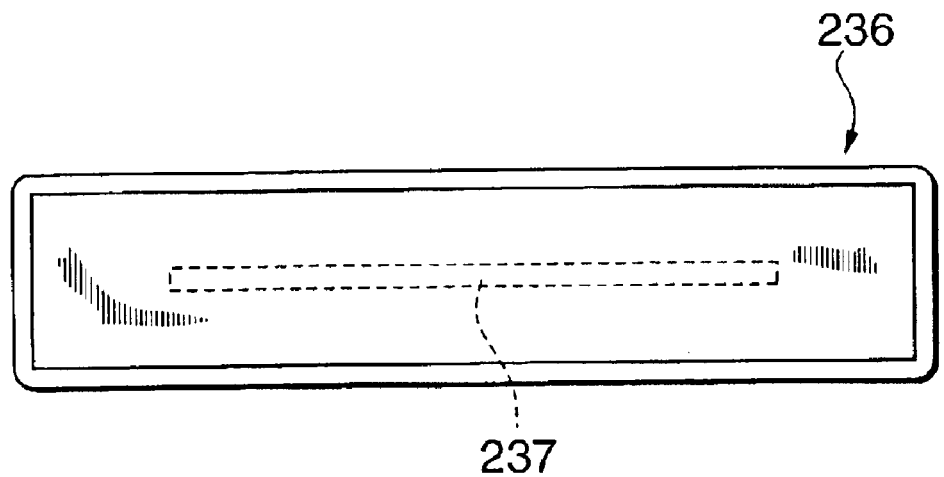
FIG. 9 is a plan view of a linear array CCD image sensor included in a measuring device for immunochromatography test pieces relating to a third embodiment.

Light exiting the cylindrical lens 133 is incident on a linear array CCD image sensor 236. The linear array CCD image sensor 236 has a light receiving face 237 extending in a one-dimensional direction, as illustrated in FIG. 9. The linear array CCD image sensor 236 is disposed in such a manner that the light receiving face 237 thereof is positioned at the point where the transmission light from the immunochromatography test piece 10 (casing 11) is formed into an image by the cylindrical lens 133. A plurality of light-receiving elements (in the present embodiment, 2048 elements) are disposed in a one-dimensional fashion on the light receiving face 237 of the linear array CCD image sensor 236. The linear array CCD image sensor 236 is fixed to a sensor holder 239 by means of a substrate 238, and this sensor holder 239 is attached to the chassis 204 via a sensor installation tube 240. As shown in FIG. 4, the direction of extension of the light receiving face 237 of the linear array CCD image sensor 236 is a direction which intersects with the generating line of the curved face of the cylindrical lens 133, when the linear array CCD image sensor 236 is installed in the chassis 204.

A baffle plate 241 for eliminating stray light is provided between the cylindrical lens 133 and the linear array CCD image sensor 236. Hole sections 242, 243 for transmitting light exiting from the cylindrical lens 133 are formed in this baffle plate 241. The baffle plate 241 is installed on the chassis 204.

The detection optical system from the aperture 134 to the linear array CCD image sensor 236 is covered by a light shielding tube 250 in order to optically shield this detection optical system. The light shielding tube 250 is installed on the chassis 204.

The measuring device 201 having the foregoing composition provides the same action and beneficial effects as the measuring devices 1, 101 relating to the first embodiment and the second embodiment and is able reliably to detect a line-shaped pattern 18 formed by coloration of an immunochromatography test piece 10, by means of the linear array CCD image sensor 236. Moreover, since light-emitting elements 21 (blue LED 21B or red LED 21R) are used as light sources, it is possible to prevent increase in the size of the measuring device 201.

Furthermore, the measuring device 201 has a cylindrical lens 133 as an imaging lens, and this cylindrical lens 133 is disposed so that the direction of the generating line of the curved face thereof intersects with the direction of travel of the antigens or antibodies in the immunochromatography test piece 10, and it forms an image of the line-shaped pattern 18 formed in a direction intersecting with the direction of travel of the antigens or antibodies, on the linear array CCD image sensor 236, due to irradiation of measurement light. Thereby, light that is parallel to the direction of travel of the antigens or antibodies in the immunochromatography test piece 10 is formed as an image on the linear array CCD image sensor 236, and light that is orthogonal to the direction of travel of the antigens or antibodies in the immunochromatography test piece 10 is defocused and equalized. Consequently, even if uneven coloration occurs in the direction of extension of the line-shaped pattern 18 formed by coloration of the immunochromatography test piece 10, this uneven coloration will be optically equalized by the cylindrical lens 133, and hence a pattern wherein uneven coloration is optically equalized will be formed as an image on the linear array CCD image sensor 236. As a result, it is possible to measure the degree of coloration of the line-shaped pattern 18 formed on the immunochromatography test piece 10 to a high level of accuracy.

Moreover, in the measuring device 201, since a lens mask 217 formed with a long rectangular slit 132 extending in the direction of the generating line of the curved face of the cylindrical lens 133 is provided at the light input face of the cylindrical lens 133, it is possible to form an image having little aberration on the linear array CCD image sensor 236.

Moreover, in the measuring device 201, since a linear array CCD image sensor 236 is used as an imaging element, a measuring device 201 having an inexpensive and compact composition can be achieved. As described above, since any unevenness in coloration is optically equalized by the cylindrical lens 133, it is possible to measure the degree of coloration of the line-shaped pattern 18 formed in the immunochromatography test piece 10 with a high level of accuracy, even if a linear array CCD image sensor 236 is used as an imaging element.

The present invention is not limited to the foregoing embodiments, and the aforementioned numerical values, and the like, can be changed appropriately.

Moreover, in the measuring devices 1, 101, 201 relating to the first embodiment to third embodiment described above, the transmission light of the measurement light irradiated onto the immunochromatography test piece 10 (casing 11) is received by a CCD image sensor 36, 236, and the light absorption of the line-shaped pattern 18 formed in the immunochromatography test piece 10 is measured on the basis of the transmission light thus received by the CCD image sensor 36, 236, but the invention is not limited to this. For example, it is also possible for the reflected light of the measurement light irradiated onto the immunochromatography test piece 10 (casing 11) to be received by the CCD image sensor 36, 236, in such a manner that the measuring devices 1, 101, 201 measure the reflectivity of the line-shaped pattern 18 formed in the immunochromatography test piece 10 on the basis of the reflected light thus received by the CCD image sensor 36, 236.

Industrial Applicability

The present invention is applicable to a measuring device for immunochromatography test pieces used in pregnancy examinations, occult blood in faeces examinations, and the like.

What is claimed is:

1. A measuring device for an immunochromatography test piece, comprising an irradiation optical system for irradiating measurement light onto said immunochromatography test piece, and a detection optical system for detecting light from said immunochromatography test piece as a result of irradiation of said measurement light;

wherein said irradiation optical system comprises a light-emitting element, and a mixing rod for mixing the light output from said light-emitting element thereinside, and irradiates the light exiting from said mixing rod onto said immunmochromatography test piece as said measurement light;

wherein said detection optical system comprises an imaging lens for forming an image of said light from said immunochromatography test piece, and an imaging element disposed in a position where said light from said immunochromatography test piece is formed into an image by said imaging lens, and detects the light transmitted by said immunochromatography test piece by means of said imaging element;

wherein said immunochromatography test piece is held in a casing having an observation window;

wherein said irradiation optical system irradiates said light emitted from said mixing rod towards said observation window, as said measurement light; and wherein the surface area of the light output face of said mixing rod is set to a larger area than the surface area of said observation window.

2. The measuring device for an immunochromatography test piece according to claim 1, wherein diffusing means for diffusing the light input to said mixing rod and the light exiting from said mixing rod are further provided on the light input face side and light output face side of said mixing rod.

* * * * *